United States Patent
Franklin

(10) Patent No.: US 12,290,273 B2
(45) Date of Patent: May 6, 2025

(54) EXTRACTION BASKET

(71) Applicant: C. R. Bard, Inc., Franklin Lakes, NJ (US)

(72) Inventor: Jeffrey Edward Franklin, Liberty Township, OH (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 849 days.

(21) Appl. No.: 17/414,272

(22) PCT Filed: Dec. 26, 2019

(86) PCT No.: PCT/US2019/068620
§ 371 (c)(1),
(2) Date: Jun. 15, 2021

(87) PCT Pub. No.: WO2020/139979
PCT Pub. Date: Jul. 2, 2020

(65) Prior Publication Data
US 2022/0061864 A1  Mar. 3, 2022

Related U.S. Application Data

(60) Provisional application No. 62/785,279, filed on Dec. 27, 2018.

(51) Int. Cl.
*A61B 17/221* (2006.01)
*A61B 17/00* (2006.01)

(52) U.S. Cl.
CPC .. *A61B 17/221* (2013.01); *A61B 2017/00862* (2013.01); *A61B 2017/2212* (2013.01); *A61B 2017/2215* (2013.01)

(58) Field of Classification Search
CPC ............ A61B 17/221; A61B 17/00862; A61B 17/00867; A61B 17/2212; A61B 17/2215;
(Continued)

(56) References Cited

U.S. PATENT DOCUMENTS 3,903,892 A  *  9/1975  Komiya ............. A61B 1/00098
                                                     606/46
6,350,266 B1     2/2002  White et al.
(Continued)

FOREIGN PATENT DOCUMENTS

CA       2371913         11/2000
CA       2371913 A1      11/2000
(Continued)

OTHER PUBLICATIONS

European Patent Office, extended European search report in EP 19903351.5, Jan. 27, 2022.
(Continued)

*Primary Examiner* — Jocelin C Tanner
(74) *Attorney, Agent, or Firm* — Rutan & Tucker LLP

(57) ABSTRACT

An example extraction device may include a generally tubular shaft including a distal end configured to be inserted into a patient and a proximal end configured to be retained exteriorly of the patient; a basket extending from the distal end of the shaft, the basket including a plurality of flexible, distally extending legs, the legs including respective distal ends that are biased generally radially outward to at least partially define a basket distal opening; a handle disposed at the proximal end of the shaft; an actuator disposed on the handle; and/or a closure line operatively coupled to the actuator, the closure line extending distally through the shaft, through a closure line guide disposed on the distal end of the shaft, and generally circumferentially about the basket distal opening, the closure line being slidably coupled to each leg near its respective leg distal end.

16 Claims, 11 Drawing Sheets

(58) Field of Classification Search
CPC ........ A61B 17/22035; A61B 17/22034; A61B 17/22
See application file for complete search history.

(56) References Cited

U.S. PATENT DOCUMENTS

| | | | |
|---|---|---|---|
| 6,383,195 B1* | 5/2002 | Richard | A61B 17/221 606/114 |
| 7,169,154 B1* | 1/2007 | Que | A61B 17/221 606/127 |
| 2002/0068944 A1 | 6/2002 | White et al. | |
| 2007/0135820 A1 | 6/2007 | Que et al. | |
| 2008/0086149 A1* | 4/2008 | Diamant | B21F 45/008 606/113 |
| 2009/0222035 A1* | 9/2009 | Schneiderman | A61B 17/221 604/264 |
| 2010/0286709 A1* | 11/2010 | Diamant | A61B 17/22022 606/128 |
| 2013/0018387 A1 | 1/2013 | Diamant | |
| 2015/0173783 A1* | 6/2015 | Tah | A61B 17/221 606/127 |
| 2018/0303499 A1 | 10/2018 | Bonneau et al. | |

FOREIGN PATENT DOCUMENTS

| | | |
|---|---|---|
| CN | 1351480 | 5/2002 |
| CN | 105828730 | 8/2016 |
| JP | 2008272501 A | 11/2008 |
| JP | 2017500156 A | 1/2017 |
| JP | 2021537855 | 9/2020 |
| WO | 0071036 A2 | 11/2000 |
| WO | 0071042 A1 | 11/2000 |
| WO | 2015100045 A1 | 7/2015 |

OTHER PUBLICATIONS

Japanese Patent Office; Partial English Language Translation of Office Action in related Japanese Patent Application No. 2021-537855, dated Sep. 20, 2022; 8 pages.

ISA/US, International Search Report in PCT/US2019/068620, Mar. 4, 2020.

WIPO, International Preliminary Report on Patentability in PCT/US2019/068620, Jun. 16, 2021.

Chinese Patent Office; Office Action in related Chinese Patent Application No. 201980093121.6 dated Dec. 6, 2023; 15 pages.

* cited by examiner

EXTRACTION BASKET

CROSS REFERENCE TO RELATED APPLICATION

This application is a U.S. national stage of International Application No. PCT/US2019/068620, filed Dec. 26, 2019, which claims the benefit of U.S. Provisional Application No. 62/785,279 filed Dec. 27, 2018, each of which is incorporated by reference in its entirety.

INTRODUCTION TO THE INVENTION

The present disclosure is directed to medical devices and instruments and, more particularly, to extraction devices that may be used to extract objects from within bodily canals and/or bodily reservoirs, for example.

The present disclosure contemplates that small stones in the distal ureter may be reliably and definitively extracted with ureteroscopic stone basketing. Presently, a wide range of ureteroscopic baskets are commercially available. Many of these ureteroscopic baskets include wires slidably mounted in a tubular sleeve forming a canula. The distal ends of the wires may have free ends or may be secured to one another and may be capable of expanding when extended outwardly by virtue of the resiliency of the material comprising the wires. For those wires that are connected to one another, a distal plug may be present at the far distal tip of the basket. Those skilled in the art have theorized that the presence of a distal tip of a basket may be disadvantageous because the tip may create distance from the end to the functional engaging portion of the basket, thus making stone entrapment more difficult. Also, those skilled in the art have lamented that certain baskets having distal tips can pierce the renal calyceal urothelial lining, thereby causing bleeding that obscures visualization and can lead to premature termination of stone extraction procedures. Similar drawbacks have been noted in the art with respect to baskets with ends that are free, an example of which is disclosed in U.S. Pat. No. 6,416,519.

The present disclosure contemplates that as a means to address the perceived drawbacks of a basket having a distal tip or with free distal ends, certain "open ended" baskets have been developed. Among these "open ended" baskets are the embodiments disclosed in U.S. Pat. No. 5,906,622. But the embodiments of U.S. Pat. No. 5,906,622 have one very pronounced disadvantage—the inability to affirmatively grab the intended object to be removed. Rather than grabbing the intended object by extending beyond and cinching around the object, the embodiments of the '622 patent operate to pinch the object from the object's sides. This pinching operation may be unsatisfactory because circumferential pressure on the baskets (which can be the result of drawing the baskets through a relatively small diameter renal conduit) of the embodiments of '622 patent may cause the object to spurt out of the distal end of the basket. In other words, the embodiments of the '622 patent may not be able to avoid distal motion of the object with respect to the basket when circumferential or proximal pressure is applied to the basket.

It is a first aspect of the present disclosure to provide an extraction device including a generally tubular shaft including a distal end configured to be inserted into a patient and a proximal end configured to be retained exteriorly of the patient; a basket extending from the distal end of the shaft, the basket including a plurality of flexible, distally extending legs, the legs including respective distal ends that are biased generally radially outward to at least partially define a basket distal opening; a handle disposed at the proximal end of the shaft; an actuator disposed on the handle; and/or a closure line operatively coupled to the actuator, the closure line extending distally through the shaft, through a closure line guide disposed on the distal end of the shaft, and generally circumferentially about the basket distal opening, the closure line being slidably coupled to each leg near its respective leg distal end. The actuator may be operative between an open position and a closed position to extend and withdraw the closure line, thereby moving the basket between an open configuration and a closed configuration, respectively.

In a more detailed embodiment of the first aspect, the extraction device may include at least one generally circumferential wall disposed on at least one of the legs. The wall may include at least one of a wire mesh and an elastomeric film. At least two of the legs may be substantially identical to each other and/or may be disposed substantially symmetrically on the shaft. The closure line guide may be generally tubular, may slidably receive the closure line therein, and/or may extends substantially from the distal end of the shaft to the distal end of one of the grasper legs. At least one of the legs may include a distally extending, lobe-shaped loop. The extraction device may include a lock on the handle, the lock being operatively coupled to the actuator to lock the actuator in at least one of an open position and a closed position. The closure line may be slidably coupled to each leg near its respective leg distal end in a draw-string fashion. The closure line guide may be flexible so that the closure line guide is bent radially inward when the basket is in the closed configuration.

It is a second aspect of the present disclosure to provide a method of operating an extraction device, the method including advancing an extraction device into a patient's body until a basket of the extraction device reaches a targeted area containing an object, the basket comprising a plurality of flexible, distally extending legs, the legs including respective distal ends that are biased generally radially outward to at least partially define a basket distal opening; manipulating the extraction device to position the object at least partially within the basket; and capturing the object by at least partially closing the basket distal opening of the basket by withdrawing proximally a closure line, the closure line extending through a closure line guide and generally circumferentially about the basket distal opening, the closure line being slidably coupled to each leg near its respective leg distal end. The closure line may draw together the leg distal ends in a draw-string fashion.

In a more detailed embodiment of the second aspect, the method may include, after capturing the object, removing the extraction device and the object from the patient's body. The method may include, prior to manipulating the extraction device to position the object at least partially within the basket, placing the basket into an open configuration by moving the closure line distally. The extraction device may include a generally tubular shaft including a distal end configured to be inserted into the patient's body and a proximal end configured to be retained exteriorly to the patient's body and/or a handle disposed at the proximal end of the shaft. The basket may extend from the distal end of the shaft. The closure line guide may be disposed on the distal end of the shaft. Withdrawing proximally the closure line may include withdrawing the closure line proximally through the closure line guide and the shaft by operating an actuator disposed on the handle. The advancing operation may include advancing the extraction device through a working channel in a ureteroscope. The extraction device may include at least one generally circumferential wall disposed on at least one of the legs. Capturing the object may include capturing the object using the at least one wall. At least partially closing the basket distal opening may include bending the closure line guide radially inward.

It is a third aspect of the present disclosure to provide an extraction device including a generally tubular shaft including a distal end configured to be inserted into a patient and a proximal end configured to be retained exteriorly of the patient; a basket extending from the distal end of the shaft, the basket including a plurality of flexible, distally extending extension legs, the extension legs including respective distal ends that are biased generally radially outward, and/or a plurality of flexible, distally extending grasper legs, each grasper leg mounted to the distal end of a respective extension leg, respective distal ends of the grasper legs at least partially defining a basket distal opening; a handle disposed at the proximal end of the shaft; a closure actuator disposed on the handle; a closure line operatively coupled to the closure actuator, the closure line extending distally through the shaft, through a closure line guide disposed on the distal end of the shaft, and generally circumferentially about the basket distal opening, the closure line being slidably coupled to each grasper leg near its respective leg distal end; and/or a retraction actuator disposed on the handle and operatively coupled to the extension legs to at least partially extend the extension legs distally from the distal end of the shaft and to retract the extension legs proximally at least partially into the shaft. The closure actuator may be operative between an open position and a closed position to extend and withdraw the closure line, thereby moving the basket between an open configuration and a closed configuration, respectively.

In a more detailed embodiment of the third aspect, the basket may include at least one generally circumferential grasper leg wall disposed on at least one of the grasper legs. The grasper leg wall may include at least one of a wire mesh and an elastomeric film. The basket may include at least one generally circumferential extension leg wall disposed on at least one of the extension legs. The extension leg wall may include at least one of a wire mesh and an elastomeric film. The closure line guide may be generally tubular, may slidably receive the closure line therein, and/or may extend substantially from the distal end of the shaft to the distal end of one of the grasper legs. The closure line may be slidably coupled to each grasper leg near its respective leg distal end in a draw-string fashion. The closure line guide may be flexible so that the closure line guide is bend radially inward when the basket is in the closed configuration.

It is a fourth aspect of the present disclosure to provide a method of operating an extraction device, the method including advancing an extraction device into a patient's body until a basket of the extraction device reaches a targeted area containing an object, the extraction device including a generally tubular shaft including a distal end configured to be inserted into the patient's body and a proximal end configured to be retained exteriorly of the patient's body, the basket extending from the distal end of the shaft, the basket comprising a plurality of flexible, distally extending extension legs, the extension legs including respective distal ends that are biased generally radially outward, and a plurality of flexible, distally extending grasper legs, each grasper leg mounted to the distal end of a respective extension leg, respective distal ends of the grasper legs at least partially defining a basket distal opening; manipulating the extraction device to position the object at least partially within the basket; capturing the object by at least partially closing the basket distal opening of the basket by withdrawing proximally a closure line, the closure line extending distally through the shaft, through a closure line guide disposed on the distal end of the shaft, and generally circumferentially about the basket distal opening, the closure line being slidably coupled to each grasper leg near its respective grasper leg distal end, the closure line drawing together the grasper leg distal ends in a draw-string fashion; and/or retracting the extension legs proximally at least partially into the shaft.

In a more detailed embodiment of the fourth aspect, the method may include, after retracting the extension legs, removing the extraction device and the object from the patient's body. The method may include, prior to manipulating the extraction device to position the object at least partially within the basket, placing the basket into an open configuration by moving the closure line distally. The extraction device may include a handle disposed at the proximal end of the shaft. Withdrawing proximally the closure line may include withdrawing the closure line proximally through the closure line guide and the shaft by operating a closure actuator disposed on the handle. Retracting the extension legs may include operating a retraction actuator disposed on the handle. The advancing operation may include advancing the extraction device through a working channel in a ureteroscope. The basket may include at least one generally circumferential grasper leg wall disposed on at least one of the grasper legs. The basket may include at least one generally circumferential extension leg wall disposed on at least one of the extension legs. Capturing the object may include capturing the object using at least one of the at least one grasper leg wall and the at least one extension leg wall. At least partially closing the basket distal opening may include bending the closure line guide radially inward.

It is a fifth aspect of the present disclosure to provide an extraction device including a generally tubular shaft including a distal end configured to be inserted into a patient and a proximal end configured to be retained exteriorly of the patient, the distal end of the shaft comprising a distal end opening; a petal grasper extending from the distal end of the shaft, the petal grasper including a plurality of distally extending petals, the petals including respective distal ends that are biased generally radially outward, the distal ends of the petals at least partially defining a grasper distal opening when the petal grasper is in an open configuration; a handle disposed at the proximal end of the shaft; an actuator disposed on the handle; and/or an actuator line operatively coupled to the actuator and the plurality of petals to move the petal grasper between the open configuration and a closed configuration in which the plurality of petals is withdrawn at least partially within the shaft at the distal end opening. In the closed configuration, the petals may substantially completely enclose an object contained therein.

In a more detailed embodiment of the fifth aspect, the petal grasper may include at least one generally circumferential wall disposed on at least one of the petals. The wall may include at least one of a wire mesh and an elastomeric film. In the closed configuration, the distal ends of the petals may substantially come into contact with one another.

It is a sixth aspect of the present disclosure to provide a method of operating an extraction device, the method including advancing an extraction device into a patient's body until a petal grasper of the extraction device reaches a targeted area containing an object, the petal grasper including a plurality of distally extending petals, the petals including respective distal ends that are biased generally radially outward, the distal ends of the petals at least partially defining a grasper distal opening when the petal grasper is in an open configuration; manipulating the extraction device to position the object at least partially within the petal grasper; and/or capturing the object by at least partially closing the distal opening of the petal grasper by withdrawing proximally an actuator line, the actuator line being operatively coupled to the plurality of petals to move the petal grasper between the open configuration and a closed configuration.

In a more detailed embodiment of the sixth aspect, the method may include, after capturing the object, removing the extraction device and the object from the patient's body. The method may include, prior to manipulating the extraction device to position the object at least partially within the petal grasper, placing the petal grasper into the open configuration. The extraction device may include a generally tubular shaft including a distal end configured to be inserted into the patient's body and a proximal end configured to be retained exteriorly to the patient's body and/or a handle disposed at the proximal end of the shaft. The petal grasper may extend from the distal end of the shaft. At least partially closing the distal opening of the petal grasper may include withdrawing the plurality of petals at least partially within the shaft at the distal end of the shaft. The advancing operation may include advancing the extraction device through a working channel in a ureteroscope. The petal grasper may include at least one generally circumferential wall disposed on at least one of the petals. Capturing the object may include capturing the object using the at least one wall.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical and surgical procedures. Of course, it will be apparent to those of ordinary skill in the art that the embodiments discussed below are examples and may be reconfigured by incorporating features across embodiments without departing from the scope and spirit of the present disclosure. To be explicitly clear, it is within the scope of the invention to combine one or more features across embodiments and the disclosure should be read with this intent. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical devices and instruments and, more particularly, extraction devices that may be used to extract objects from within bodily canals and/or bodily reservoirs.

Figure 1:
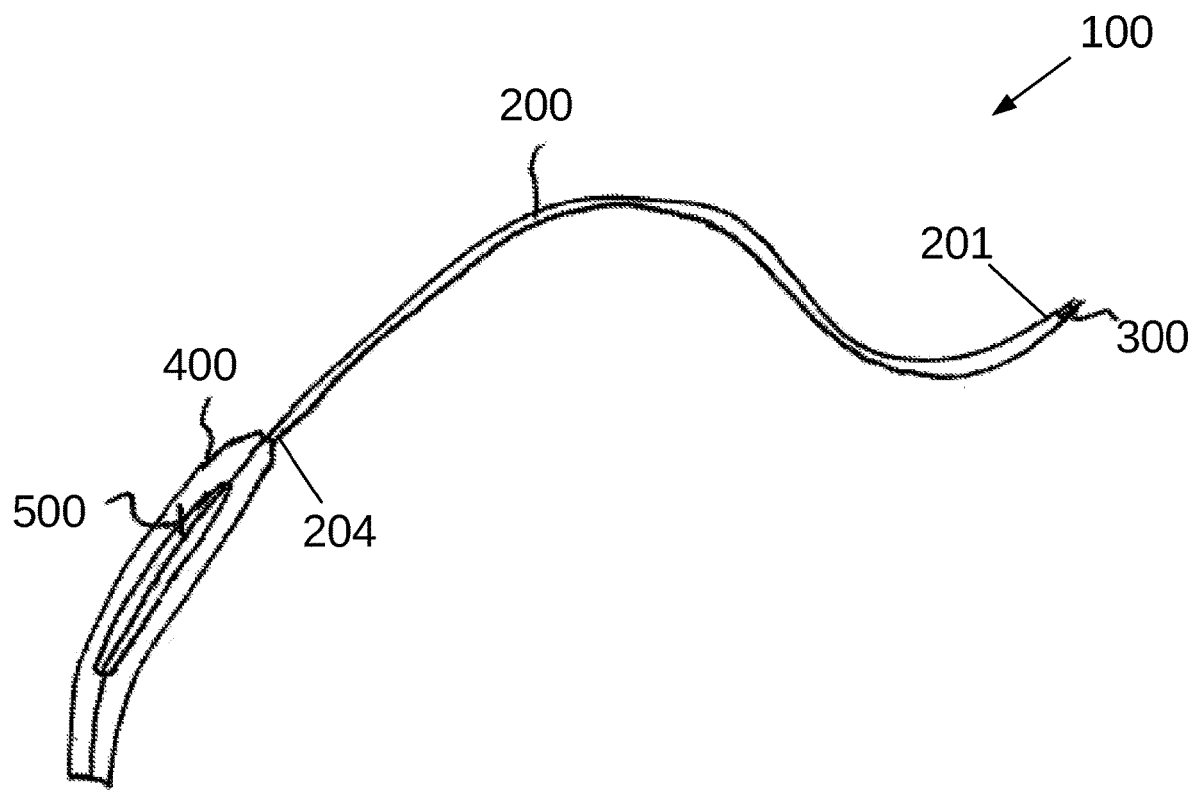
FIG. 1 is an elevated perspective view of an example extraction device.

FIG. 1 is an elevated perspective view of an example extraction device 100 according to at least some aspects of the present disclosure. Extraction device 100 may include a shaft 200, which may be in the form of an elongated, hollow, generally tubular sheath. Shaft 200 may be generally configured for its distal end 201 to be inserted into a patient and its proximal end 204 to be retained exteriorly of the patient. A reconfigurable basket 300 may be disposed at the distal end 201 of shaft 200. A handle 400 may be disposed at the proximal end 204 of shaft 200. An actuator 500 may be movably disposed on handle 400 and/or may be operatively coupled to basket 300. As used herein, "distal" may refer to a direction generally toward basket 300 and "proximal" may refer to a direction generally toward handle 400.

Figure 2:
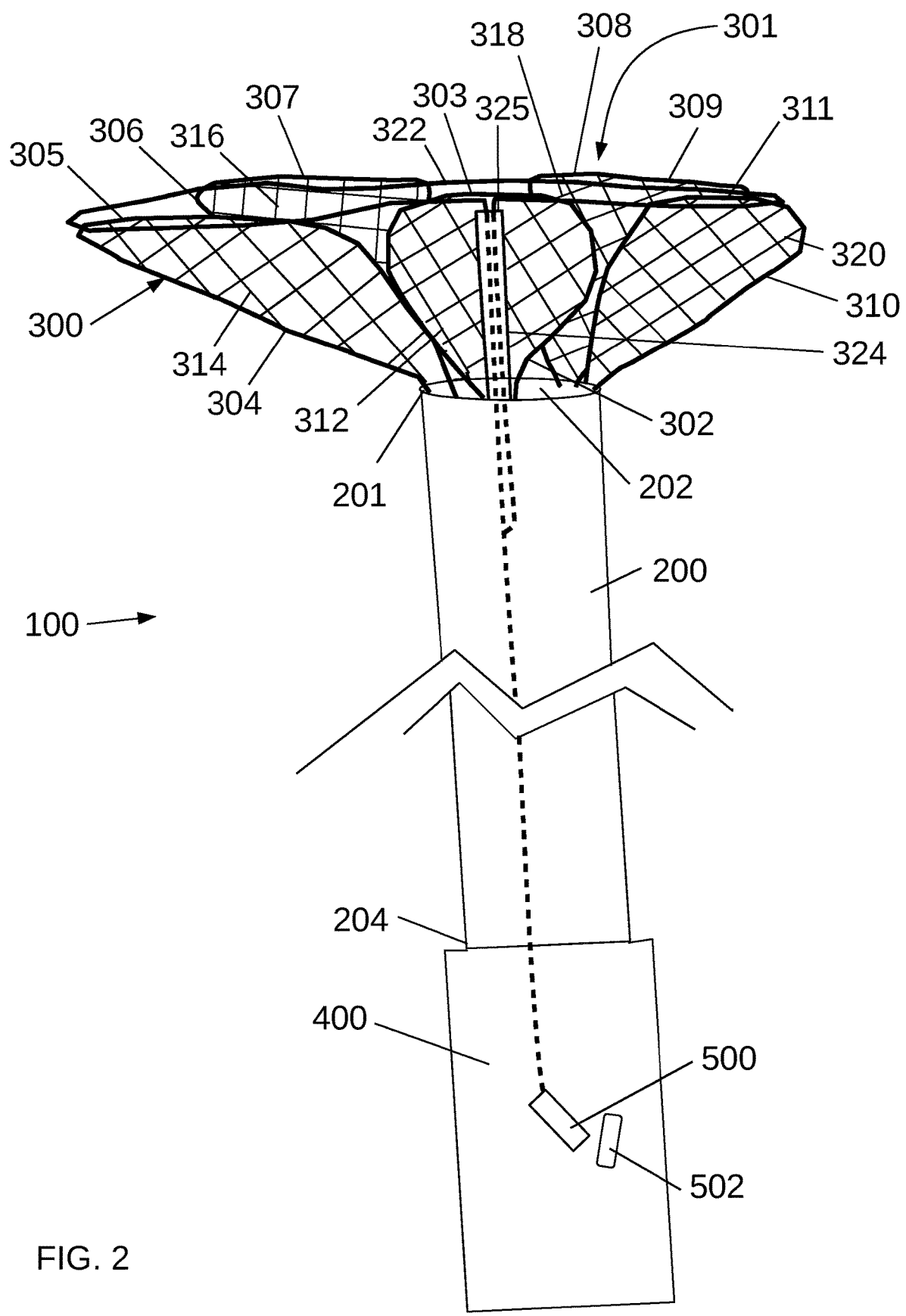
FIG. 2 is a detailed perspective view of an example extraction device with an example basket in an open configuration.
Figure 3:
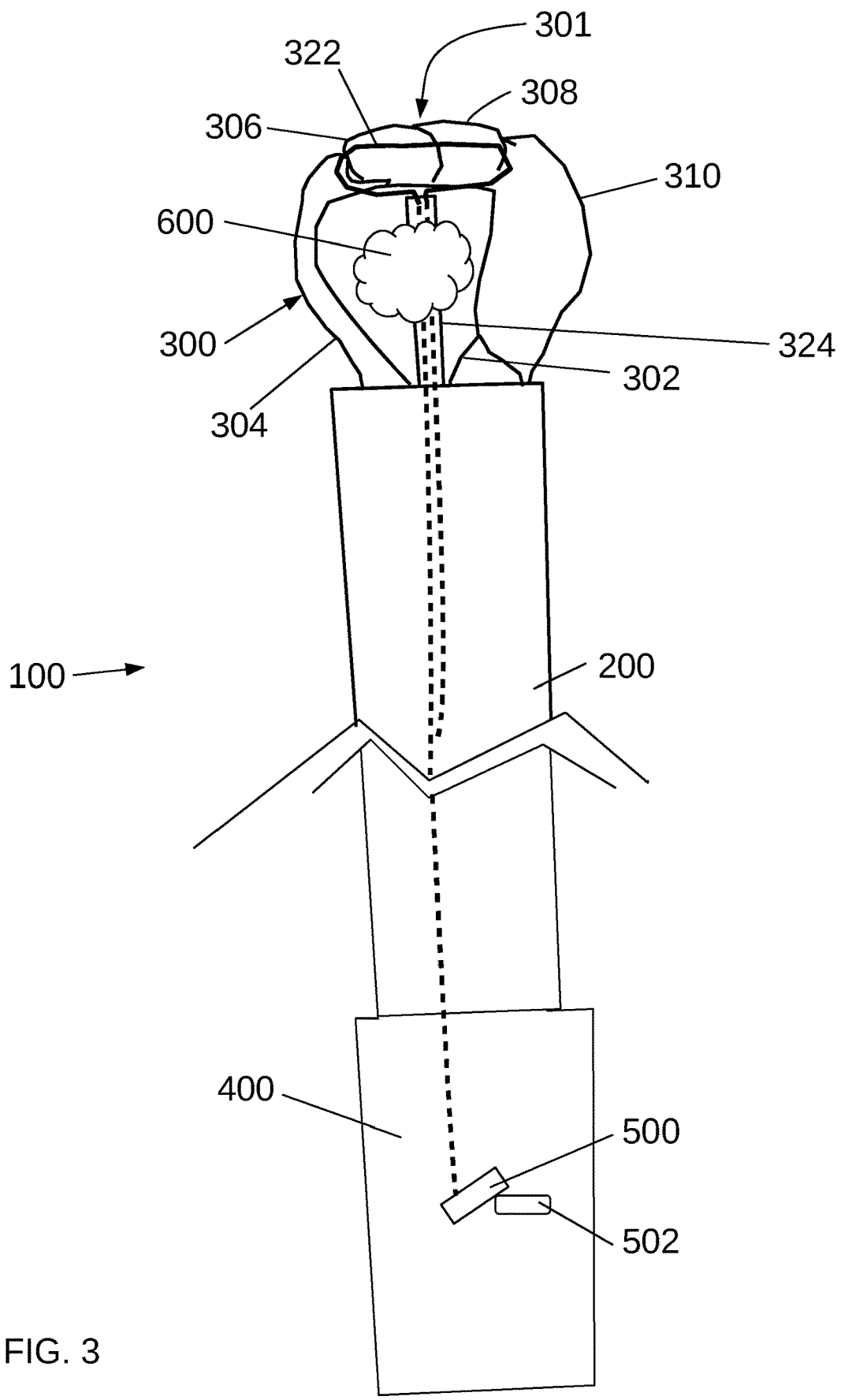
FIG. 3 is a detailed perspective view of an example extraction device with an example basket in a closed configuration.

FIGS. 2 and 3 are detailed perspective views of an example extraction device 100 with basket 300 in open and closed configurations, respectively, according to at least some aspects of the present disclosure. In some example embodiments, basket 300 may include two or more legs 302, 304, 306, 308, 310. Legs 302, 304, 306, 308, 310 may be mounted to shaft 200 at or near a shaft distal end opening 202. For example, legs 302, 304, 306, 308, 310 may be generally evenly circumferentially spaced apart and/or may be mounted within shaft distal end opening 202. Legs 302, 304, 306, 308, 310 may be flexible (compare FIGS. 2 and 3) and/or may be biased to the open configuration (FIG. 2). For example, legs 302, 304, 306, 308, 310 may be formed such that their respective distal ends 303, 305, 307, 309, 311 are biased generally radially outward (e.g., biased open) to form a basket distal opening 301. In some example embodiments, legs 302, 304, 306, 308, 310 may be constructed at least partially from spring grade stainless steel and/or nickel titanium alloys (e.g., nitinol) in the super elastic range, for example.

Referring to FIG. 2, some example embodiments may include walls 312, 314, 316, 318, 320 disposed on respective legs 302, 304, 306, 308, 310. For example, a leg 302, 304, 306, 308, 310 that is formed generally as a distally extending loop in a lobed shape may have a wall 312, 314, 316, 318, 320 disposed generally within the lobed shaped loop in a generally circumferential fashion. In some example embodiments, walls 312, 314, 316, 318, 320 may be constructed from a mesh (e.g., metal wire mesh) and/or an elastomeric film (e.g., which may be laser cut and/or may be porous).

Referring to FIGS. 2 and 3, in some example embodiments according to at least some aspects of the present disclosure, basket 300 may include a closure line 322, which may extend generally circumferentially about the basket distal opening 301, such as near distal ends 303, 305, 307, 309, 311 of some or all legs 302, 304, 306, 308, 310. Closure line 322 may be operatively coupled to some or all of legs 302, 304, 306, 308, 310, such as by being slidably attached to distal ends 303, 305, 307, 309, 311 in a draw-string (e.g., purse-string) fashion. For example, closure line 322 may a run generally circumferentially around basket 300 near distal ends 303, 305, 307, 309, 311 of legs 302, 304, 306, 308, 310 in a generally circular path so that when closure line 322 is drawn tight, the distal ends 303, 305, 307, 309, 311 are drawn together and/or closed, thus at least partially closing basket distal end opening 301.

In some example embodiments, closure line 322 may extend from legs 302, 304, 306, 308, 310, through a closure line guide 324, which may be disposed on at least one of a leg 302, 304, 306, 308, 310 and/or shaft 200, such as near shaft distal end opening 202. Closure line guide 324 may extend generally distally from shaft distal end opening 202 to near distal end 303 of leg 302, for example. Closure line guide 324 may include a closure line guide distal end opening 325 through which closure line 322 may extend generally circumferentially outward about distal ends 303, 305, 307, 309, 311 of legs 302, 304, 306, 308, 310. In some example embodiments, closure line guide 324 may be generally tubular (e.g., may have a longitudinal channel therethrough). In some example embodiments, closure line guide 324 may be generally flexible (e.g., generally as flexible as legs 302, 304, 306, 308, 310) such that it bends radially inward in the closed configuration (FIG. 3).

In some example embodiments, closure line 322 may be operatively coupled to actuator 500 and/or may extend from handle 400, distally through shaft 200, distally through closure line guide 324, and outward through closure line guide distal end opening 325.

In some example embodiments, actuator 500 may be configured for operation by a user, such as by rotating, sliding, and/or pivoting, to extend and/or withdraw closure line 322 to open and/or close basket 300. In some example embodiments, when basket 300 is in the open configuration (FIG. 2), operating actuator 500 from an open position (FIG. 2) towards a closed position (FIG. 3) may pull closure line 322 proximally through shaft 200, which may draw distal ends 303, 305, 307, 309, 311 of legs 302, 304, 306, 308, 310 radially inward, generally in a draw-string (e.g., pursestring) fashion, thereby substantially reducing and/or at least partially closing basket distal end opening 301.

Some example embodiments may include a lock 502 on handle 400, which may be operatively coupled to actuator 500 to lock actuator 500 in an open position, in a fully closed position, and/or in between the open position and the closed position (e.g., in a partially closed position).

In some example embodiments, in a fully closed configuration, walls 312, 314, 316, 318, 320 may substantially completely enclose (e.g., encapsulate) object 600 held within basket 300. In some example embodiments, in a fully closed configuration, walls 312, 314, 316, 318, 320 may partially enclose object 600 held within basket 300. In some example embodiments, in a partially closed configuration, walls 312, 314, 316, 318, 320 may partially enclose object 600 held within basket 300.

In some example embodiments, when basket 300 is in the closed configuration (FIG. 3), operating actuator 500 from the closed configuration (FIG. 3) towards the open configuration (FIG. 2) may allow distal movement of closure line 322, which may be tensioned distally by the opening bias of legs 302, 304, 306, 308, 310. Movement of closure line 322 distally may allow distal ends 303, 305, 307, 309, 311 of legs 302, 304, 306, 308, 310 to move radially outward, generally circumferentially expanding and/or opening basket distal end opening 301.

In some example embodiments, legs 302, 304, 306, 308, 310 and/or walls 312, 314, 316, 318, 320 may be substantially identical to each other and/or may be arranged generally symmetrically about shaft distal end opening 202. In some example embodiments, one or more legs 302, 304, 306, 308, 310 and/or walls 312, 314, 316, 318, 320 may differ from the others and/or may be arranged generally asymmetrically about shaft distal end opening 202.

Referring to FIGS. 1-3, an example method of operating an extraction device 100 including a basket 300 is described. Extraction device 100 may be utilized to extract various objects 600 from within an interior of an anatomical cavity. As an example, use of extraction device 100 will be explained in the context of a kidney stone removal procedure. Nevertheless, those skilled in the art will understand that use of the extraction device 100 is not limited to kidney stone removal procedures, but rather that this description is just one of numerous procedures for which the extraction device 100 has application.

In some example methods, a suitable path to the kidney stone in the patient's body is established, and appropriate visualization may also be established, such as by means of a ureteroscope. Thereafter, extraction device 100 is advanced until basket 300 reaches the targeted area where object 600 to be removed is located. In some example embodiments, this advance may be accomplished by manually feeding shaft 200 through a working channel in the ureteroscope.

Upon reaching object 600, basket 300 is placed in the open configuration (FIG. 2), if it is not already in the open configuration. For example, in some circumstances it may be desirable to insert extraction device 100 with basket 300 in the closed configuration. Then, extraction device 100 may be manipulated to position object 600 (e.g., a kidney stone) at least partially within basket 300. Then, actuator 500 may be operated to withdraw proximally closure line 322, which may draw distal ends 303, 305, 307, 309, 311 together and/or closed, thus at least partially closing basket distal end opening 301 and/or at least partially capturing object 600 within basket 300 (FIG. 3). With object 600 retained basket 300, extraction device 100 may be removed from the patient, thereby removing object 600 from the patient.

Figure 4:
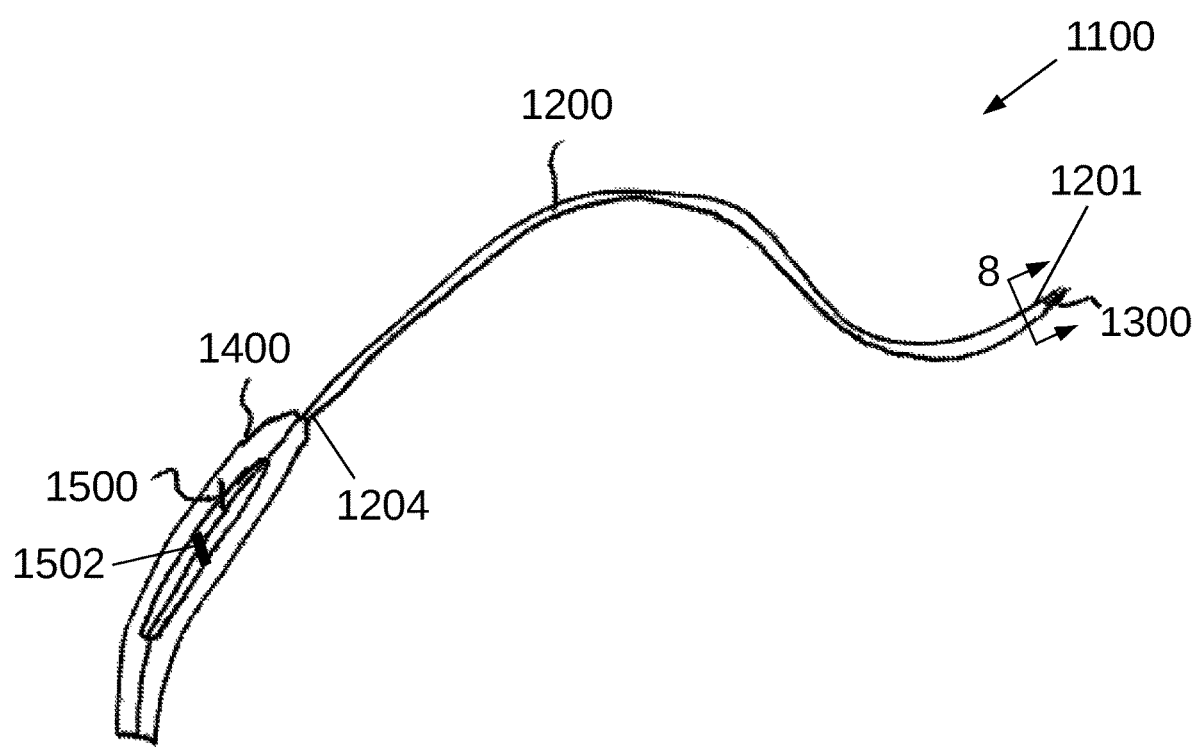
FIG. 4 is an elevated perspective view of an example extraction device including an example dual-mode basket.

FIG. 4 is an elevated perspective view of an example extraction device 1100 including a dual-mode basket 1300 according to at least some aspects of the present disclosure. Extraction device 1100 may include a shaft 1200, which may be in the form of an elongated, hollow, generally tubular sheath. Shaft 1200 may be generally configured for its distal end 1201 to be inserted into a patient and its proximal end 1204 to be retained exteriorly of the patient. A reconfigurable basket 1300 may be disposed at the distal end 1201 of shaft 1200. A handle 1400 may be disposed at the proximal end 1204 of shaft 1200. A closure actuator 1500 and/or a retraction actuator 1502 may be movably disposed on handle 1400 and/or may be operatively coupled to basket 1300.

Figure 5:
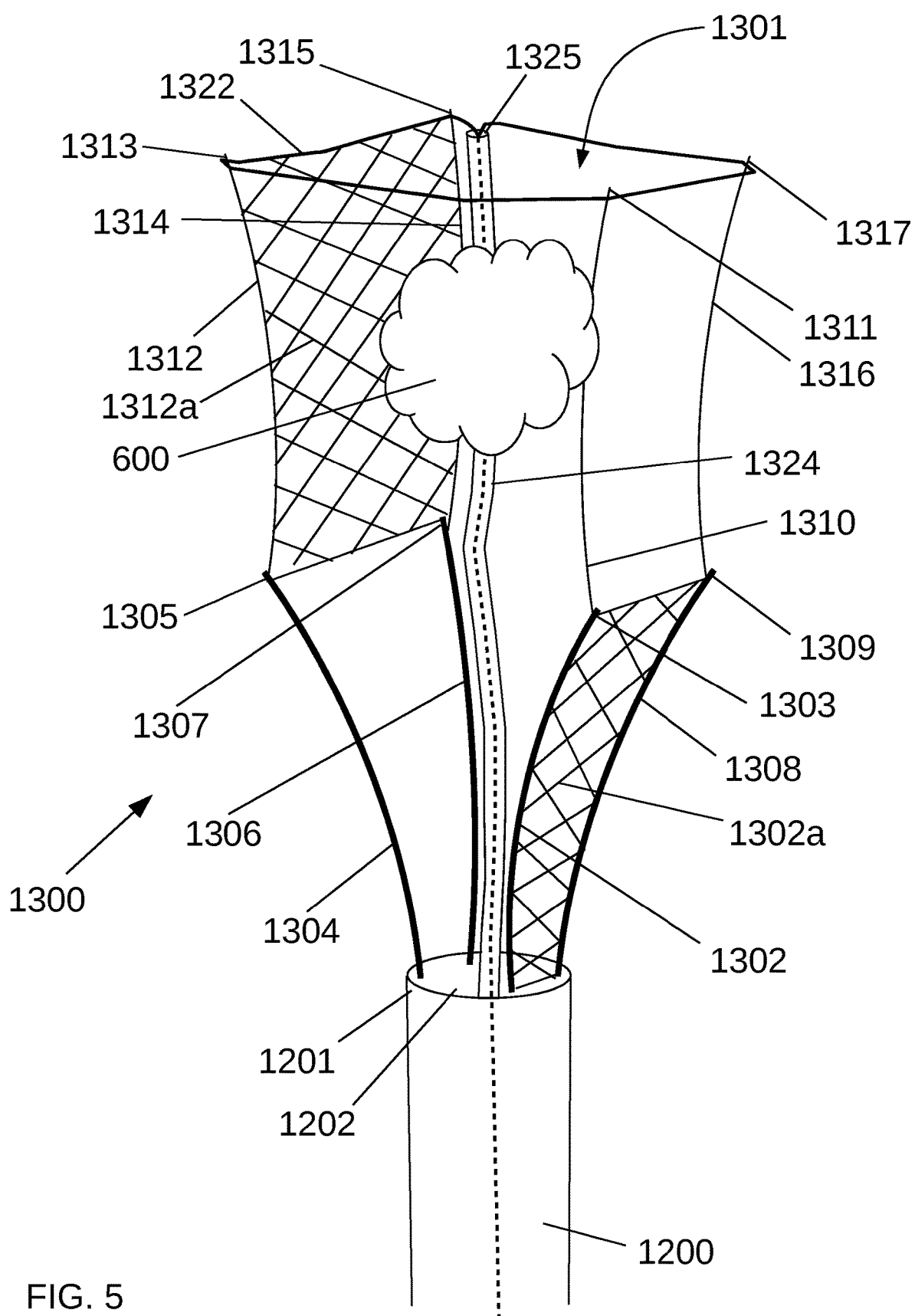
FIG. 5 is a detailed perspective view of an example dual-mode basket in an open configuration.
Figure 6:
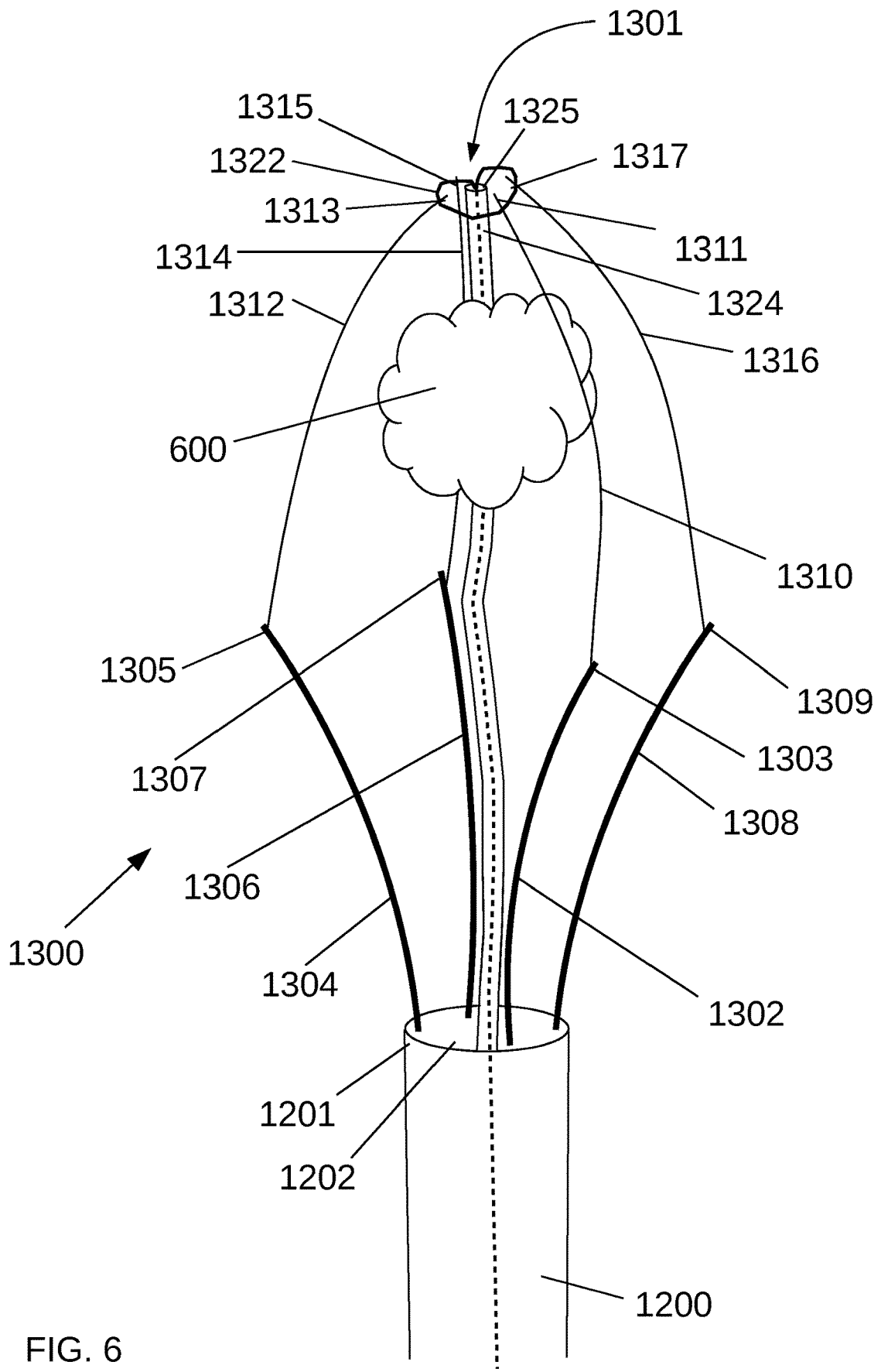
FIG. 6 is a detailed perspective view of an example dual-mode basket in a closed configuration.
Figure 7:
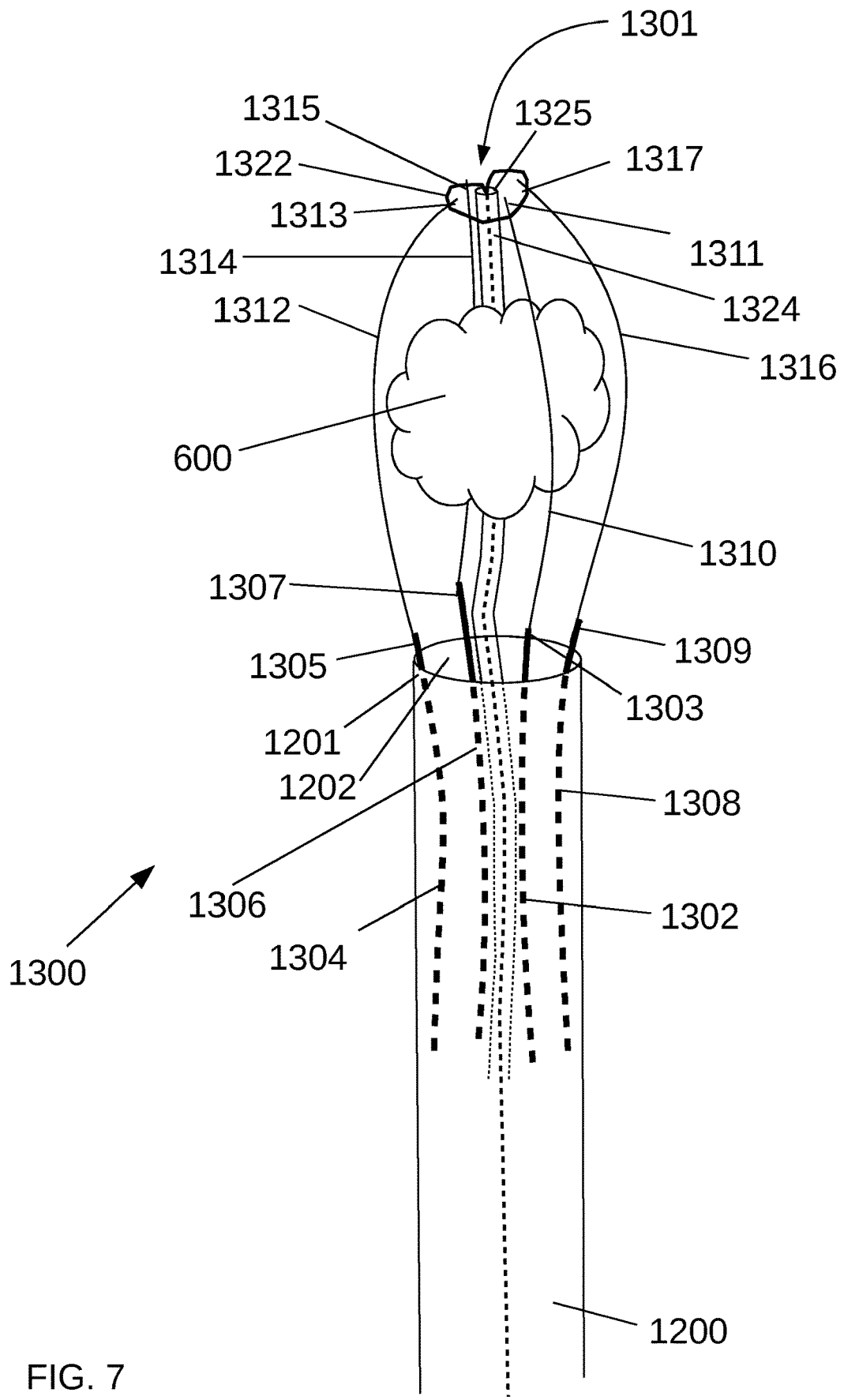
FIG. 7 is a detailed perspective view of an example dual-mode basket in a retracted configuration.

FIGS. 5-7 are detailed perspective views of an example dual-mode basket 1300 in an open configuration, a closed configuration, and a retracted configuration, respectively, according to at least some aspects of the present disclosure. In some example embodiments, dual-mode basket 1300 may be disposed at distal end 1201 of shaft 1200. Dual-mode basket 1300 may include two or more extension legs 1302, 1304, 1306, 1308, which may be axially (longitudinally) slidably mounted to shaft 1200 at or near a shaft distal end opening 1202. For example, extension legs 1302, 1304, 1306, 1308 may be generally evenly circumferentially spaced apart and/or may be partially disposed within shaft distal end opening 1202. Extension legs 1302, 1304, 1306, 1308 may be flexible (compare FIGS. 5 and 7) and/or may be biased to the open configuration (FIG. 5). For example, extension legs 1302, 1304, 1306, 1308 may be formed such that their respective distal ends 1303, 1305, 1307, 1309 are biased generally radially outward (e.g., biased open). In some example embodiments, extension legs 1302, 1304, 1306, 1308 may be constructed at least partially from spring grade stainless steel and/or nickel titanium alloys (e.g., nitinol) in the super elastic range, for example.

In some example embodiments, dual-mode basket 1300 may include two or more grasper legs 1310, 1312, 1314, 1316, which may extend distally from distal ends 1303, 1305, 1307, 1309 of respective extension legs 1302, 1304, 1306, 1308. Grasper legs 1310, 1312, 1314, 1316 may be flexible (compare FIGS. 5 and 6) and/or may be biased to the open configuration (FIG. 5). For example, grasper legs 1310, 1312, 1314, 1316 may be formed such that their respective distal ends 1311, 1313, 1315, 1317 are biased generally radially outward (e.g., biased open). Grasper legs 1310, 1312, 1314, 1316 may be formed such that their respective distal ends 1311, 1313, 1315, 1317 are biased generally radially outward (e.g., biased open) to form a basket distal opening 1301. In some example embodiments, grasper legs 1310, 1312, 1314, 1316 may be constructed at least partially from spring grade stainless steel and/or nickel titanium alloys (e.g., nitinol) in the super elastic range, for example.

In some example embodiments, dual-mode basket 1300 may include a closure line 1322 extending generally circumferentially about the basket distal opening 1301, such as near distal ends 1311, 1313, 1315, 1317 of some or all grasper legs 1310, 1312, 1314, 1316. Closure line 1322 may be operatively coupled to some or all of legs grasper legs 1310, 1312, 1314, 1316, such as by being slidably attached to distal ends 1311, 1313, 1315, 1317 in a draw-string (e.g., purse-string) fashion. For example, closure line 1322 may a run generally circumferentially around basket 1300 near distal ends 1311, 1313, 1315, 1317 of grasper legs 1310, 1312, 1314, 1316 in a generally circular path so that when closure line 1322 is drawn tight, the distal ends 1311, 1313, 1315, 1317 are drawn together and/or closed, thus at least partially closing basket distal end opening 1301 (FIGS. 6 and 7).

Referring to FIGS. 5-7, in some example embodiments, closure line 1322 may extend from grasper legs 1310, 1312, 1314, 1316, through a closure line guide 1324, which may be disposed on at least one of an extension leg 1302, 1304, 1306, 1308, a grasper leg 1310, 1312, 1314, 1316, and/or shaft 1200, such as near shaft distal end opening 1202. Closure line guide 1324 may extend generally distally from shaft distal end opening 1202 to near distal end 1315 of leg 1314, for example. Closure line guide 1324 may include a closure line guide distal end opening 1325 through which closure line 1322 may extend generally circumferentially outward about distal ends 1311, 1313, 1315, 1317 of grasper legs 1310, 1312, 1314, 1316. In some example embodiments, closure line guide 1324 may be generally tubular (e.g., may have a longitudinal channel therethrough). In some example embodiments, closure line guide 1324 may be generally flexible (e.g., generally as flexible as grasper legs 1310, 1312, 1314, 1316 and/or extension legs 1302, 1304, 1306, 1308) such that it bends (e.g., radially inward) as required in the closed configuration (FIG. 6) and/or the retracted configuration (FIG. 7).

Figure 8:
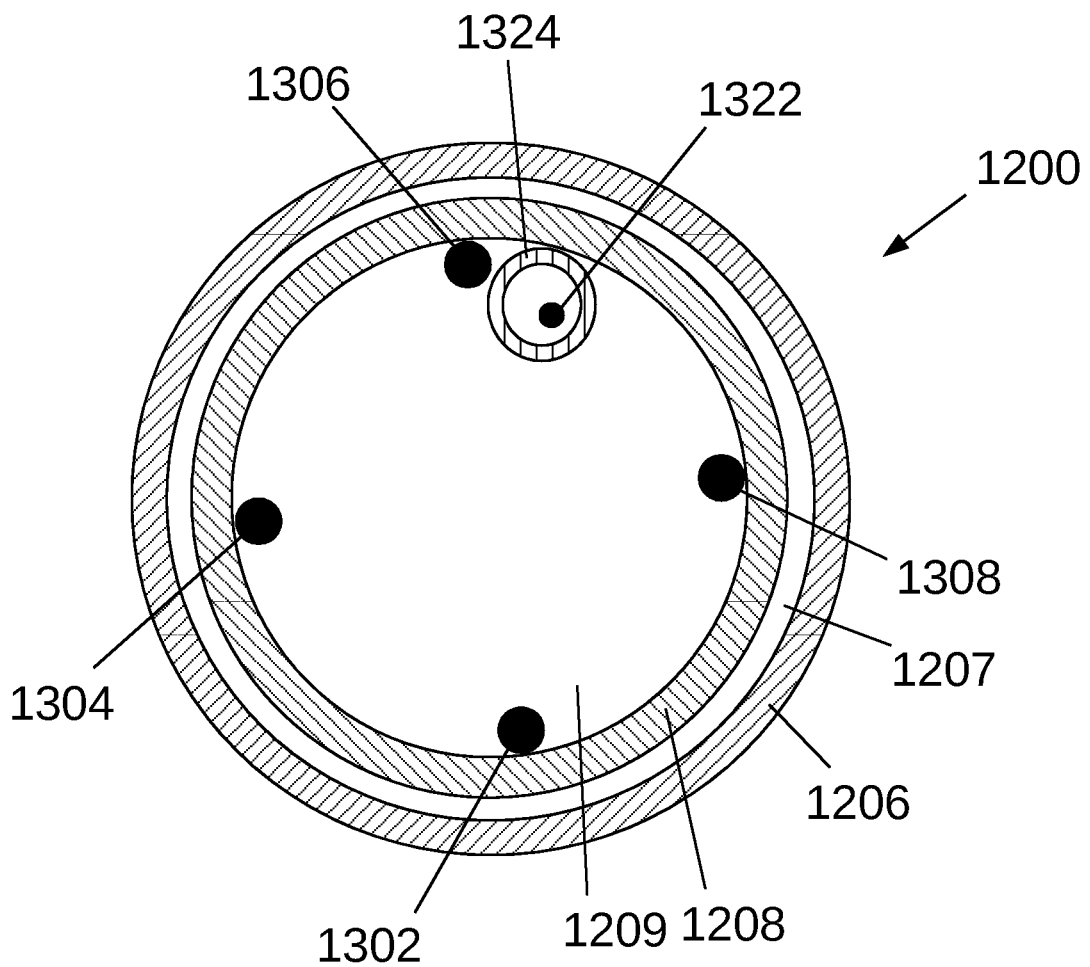
FIG. 8 is a cross section view of an example shaft of a dual-mode basket extraction device.

FIG. 8 is a cross section view of an example shaft 1200 of a dual-mode basket 1300 extraction device 1100, according to at least some aspects of the present disclosure. Shaft 1200 may be utilized in some example extraction devices, such as extraction device 1100 including dual-mode basket 1300. In some example embodiments, shaft 1200 may include an outer sheath 1206, which may be generally tubular and/or may define a longitudinal cavity 1207 therein. A generally tubular conduit 1208 may be slidably disposed within cavity 1207 of outer sheath 1206. Conduit 1208 may be generally tubular and/or may define a longitudinal cavity 1209 therein. Conduit 1208 may be axially (e.g., longitudinally) slidable relative to outer sheath 1206, such as proximally and distally. Extension legs 1302, 1304, 1306, 1308 may be mounted to conduit 1208, such as within cavity 1209. Closure line guide 1324, which may include closure line 1322 extending therethrough, may extend within cavity 1209 of conduit 1208.

Referring to FIGS. 4-8, in some example embodiments, closure line 1322 may be operatively coupled to closure actuator 1500 and/or may extend from handle 1400, distally through shaft 1200, distally through closure line guide 1324, and outward through closure line guide distal end opening 1325. In some example embodiments, closure actuator 1500 may be configured for operation by a user, such as by rotating, sliding, and/or pivoting, to extend or withdraw closure line 1322 to open and/or close basket 1300. In some example embodiments, when basket 1300 is in the open configuration (FIG. 5), operating closure actuator 1500 from an open position towards a closed position may pull closure line 1322 proximally through shaft 1200, which may draw distal ends 1311, 1313, 1315, 1317 of grasper legs 1310, 1312, 1314, 1316 radially inward, generally in a draw-string (e.g., purse-string) fashion, generally reducing and/or at least partially closing basket distal end opening 1301 (FIG. 6).

In some example embodiments, when dual-mode basket 1300 is in the closed configuration (FIG. 6) and/or the retracted configuration (FIG. 7), operating closure actuator 1500 from the closed position towards the open position may allow distal movement of closure line 1322, which may be tensioned distally by the opening bias of grasper legs 1310, 1312, 1314, 1316 and/or extension legs 1302, 1304, 1306, 1308. Movement of closure line 1322 distally may allow distal ends 1311, 1313, 1315, 1317 of grasper legs 1310, 1312, 1314, 1316 to move radially outward, generally circumferentially expanding and/or opening basket distal end opening 1301 (FIG. 6).

In some example embodiments, extension legs 1302, 1304, 1306, 1308 may be axially (longitudinally) slidable relative to shaft 1200. For example, extension legs 1302, 1304, 1306, 1308 may be mounted to conduit 1208, which may be slidably disposed within shaft 1200 (FIG. 8). Referring to FIG. 6, in an example extended configuration, extension legs 1302, 1304, 1306, 1308 may extend distally from shaft distal end opening 1202. Referring to FIG. 7, in an example retracted configuration, extension legs 1302, 1304, 1306, 1308 may be at least partially contained within shaft 1202. For example, extension legs 1302, 1304, 1306, 1308 may be substantially contained within shaft with only relatively short portions near distal ends 1303, 1305, 1307, 1309 of respective extension legs 1302, 1304, 1306, 1308 extending distally from shaft distal end opening 1202.

In some example embodiments, retracting extension legs 1302, 1304, 1306, 1308 at least partially into shaft 1202 may cause distal ends 1303, 1305, 1307, 1309 of extension legs 1302, 1304, 1306, 1308 to move radially closer (FIG. 7).

Extending extension legs 1302, 1304, 1306, 1308 at least partially out of shaft 1202 may allow distal ends 1303, 1305, 1307, 1309 of extension legs 1302, 1304, 1306, 1308 to move radially farther apart, such as by the biased-open nature of extension legs 1302, 1304, 1306, 1308 (FIGS. 5 and 6).

In some example embodiments, retraction actuator 1502 on handle 1400 may be repositionable with respect to handle 1400 to extend (FIGS. 5 and 6) and/or retract (FIG. 7) extension legs 1302, 1304, 1306, 1308 relative to shaft 1200. Referring to FIG. 8, for example, retraction actuator 1502 may be operatively coupled to conduit 1208, to which extension legs 1302, 1304, 1306, 1308 may be mounted. Conduit 1208 may have an external maximum dimension that is smaller than the smallest internal dimension of sheath 1206, thereby allowing conduit 1208 to be longitudinally repositionable with respect to sheath 1206. In some example embodiments, closure line 1322, may be independently longitudinally repositionable with respect to conduit 1208 and/or sheath 1206, such as by the action of closure actuator 1500. Similarly, conduit 1208 may be independently longitudinally repositionable with respect to closure line 1322 and/or sheath 1206, such as by the action of retraction actuator 1502. In this fashion, motion of retraction actuator 1502 with respect to handle 1400 may be operative to transmit corresponding longitudinal motion to conduit 1208 within sheath 1206, which causes corresponding longitudinal motion (extension and/or retraction) of extension legs 1302, 1304, 1306, 1308. In some example embodiments, travel of retraction actuator 1502 may be limited so that its range of motion corresponds with the range of extending and retracting extension legs 1302, 1304, 1306, 1308. In other words, when retraction actuator 1502 is at one end of its range of motion, extension legs 1302, 1304, 1306, 1308 may be in the retracted configuration (FIG. 7) and/or extension legs 1302, 1304, 1306, 1308 may be in the extended configuration (FIGS. 5 and 6) when retraction actuator 1502 is at the opposite end of its range of motion.

Referring to FIGS. 4-8, an example method of operating an extraction device 1100 including a dual-mode basket 1300 is described. Extraction device 1100 including dual-mode basket 1300 may be utilized to extract various objects 600 from within an interior of an anatomical cavity. As an example, use of extraction device 1100 including a dual-mode basket 1300 will be explained in the context of a kidney stone removal procedure. Nevertheless, those skilled in the art will understand that use of the extraction device 1100 including a dual-mode basket 1300 is not limited to kidney stone removal procedures, but rather that this description is just one of numerous procedures for which the extraction device 1100 including dual-mode basket 1300 has application.

In some example methods, a suitable path to the kidney stone in the patient's body is established, and appropriate visualization may also be established, such as by means of a ureteroscope. Thereafter, dual-mode basket 1300 of extraction device 1100 is advanced until dual-mode basket 1300 of extraction device 1100 reaches the targeted area where object 600 to be removed is located. In some example embodiments, this advance may be accomplished by manually feeding shaft 1200 through a working channel in the ureteroscope.

Upon reaching object 600, dual-mode basket 1300 is place in the open configuration (FIG. 5), if it is not already in the open configuration. For example, in some circumstances it may be desirable to insert extraction device 1100 with dual-mode basket 1300 in the closed configuration and/or the retracted configuration. Then, extraction device 1100 may be manipulated to position object 600 (e.g., a kidney stone) generally within dual-mode basket 1300 (FIG. 5). Then, closure actuator 1500 may be operated to withdraw proximally closure line 1322, which may draw distal ends 1311, 1313, 1315, 1317 together and/or closed, thus at least partially closing basket distal end opening 1301 and/or at least partially capturing object 600 within dual-mode basket 1300 (FIG. 6). Then, retraction actuator 1502 may be operated to at least partially retract extension legs 1302, 1304, 1306, 1308 (FIG. 7). With object 600 retained within dual-mode basket 1300, extraction device 1100 may be removed from the patient, thereby removing object 600 from the patient.

Referring to FIG. 5, some example embodiments may include one or more nets or walls disposed on one or more of extension legs 1302, 1304, 1306, 1308 and/or grasper legs 1310, 1312, 1314, 1316. For example, FIG. 5 illustrates a net or wall 1312*a* disposed on grasper legs 1312, 1314 and a net or wall 1302*a* disposed on extension legs 1302, 1308. Although the nets or walls are omitted from several of the other figures for clarity and are shown only on some extension legs and grasper legs in FIG. 5, it is within the scope of the disclosure to include nets or walls on any or all extension legs and/or on any or all grasper legs. In some example embodiments, the walls and/or the net (e.g., nets or walls 1312*a*, 1302*a*) may be constructed from a mesh (e.g., metal wire mesh) and/or an elastomeric film (e.g., which may be laser cut and/or may be porous).

Figure 9:
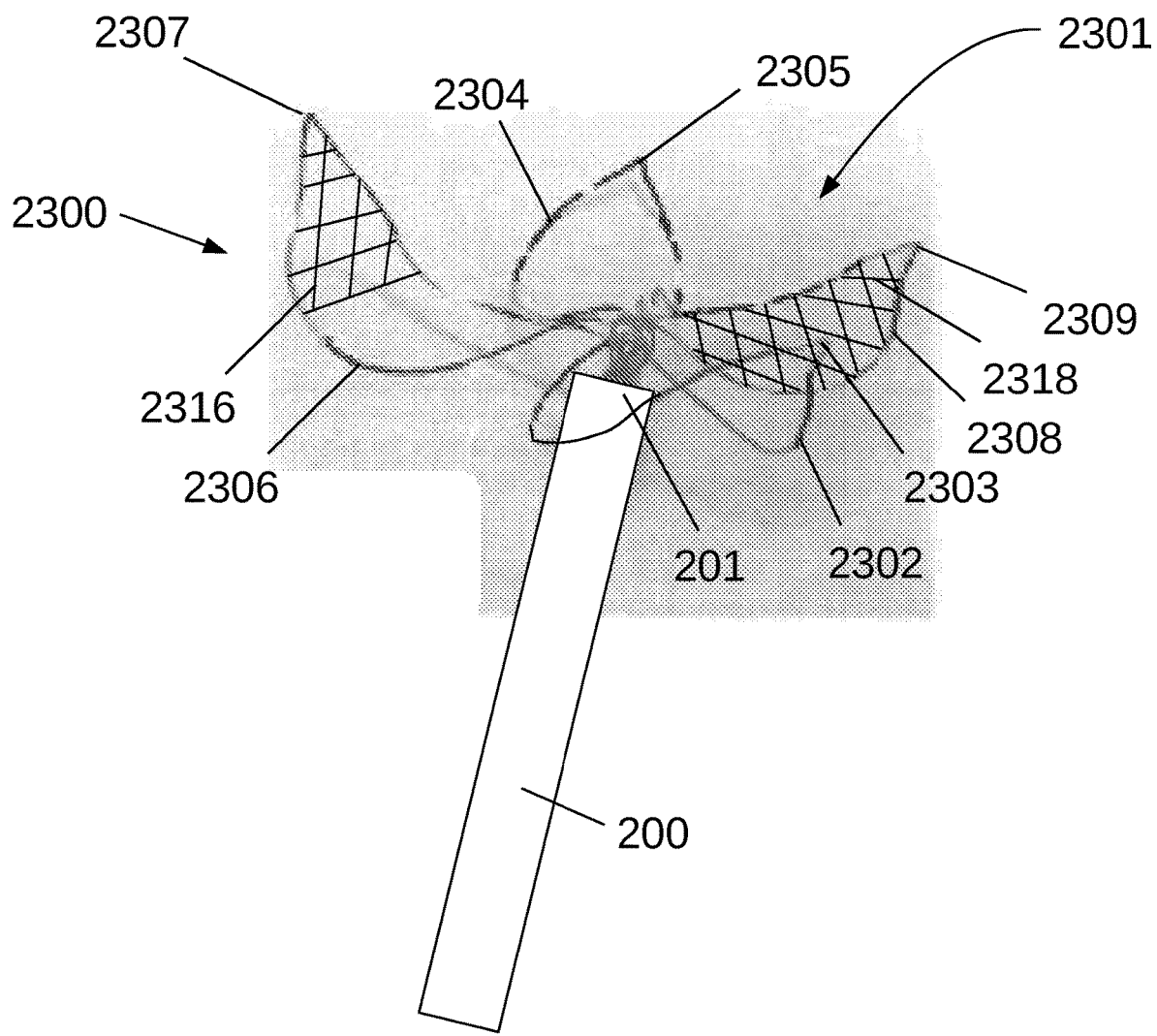
FIG. 9 is a detailed perspective view of an alternative example basket in the form of a petal grasper in an open configuration.
Figure 10:
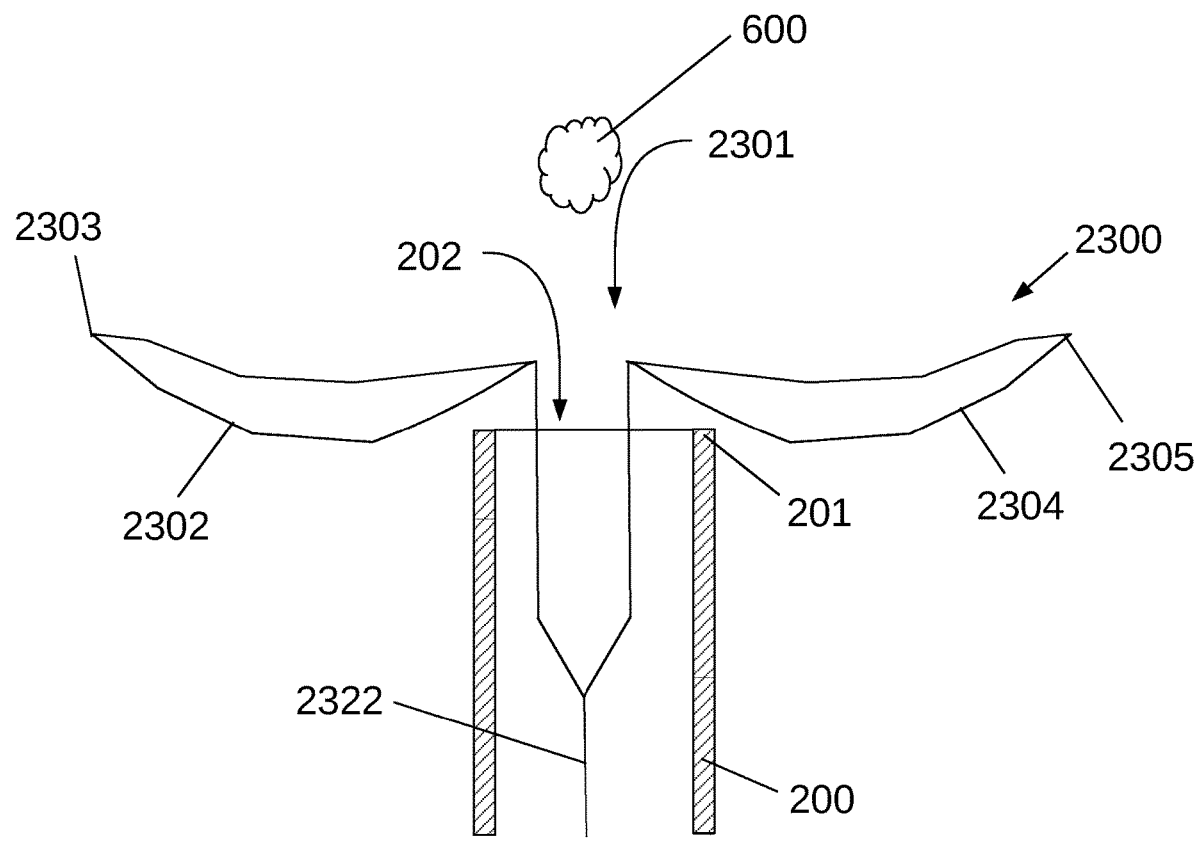
FIG. 10 is a section view of an example petal grasper in an open configuration.
Figure 11:
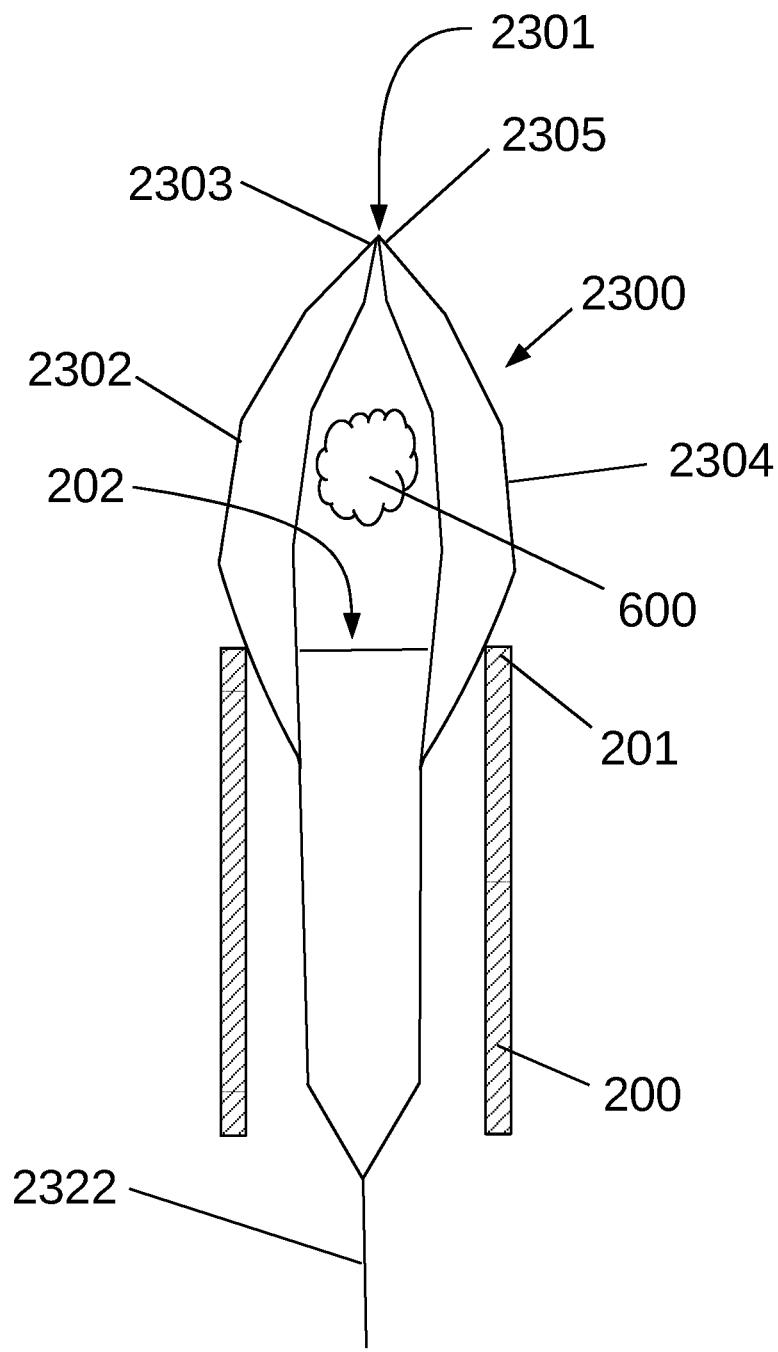
FIG. 11 is a section view of an example petal grasper in a closed configuration; all in accordance with at least some aspects of the present disclosure.

FIG. 9 is a detailed perspective view of an alternative example basket in the form of a petal grasper 2300 in an open configuration, according to at least some aspects of the present disclosure. FIGS. 10 and 11 are section views of an example petal grasper 2300 in an open configuration and a closed configuration, respectively, according to at least some aspects of the present disclosure. Generally, petal grasper 2300 may be an alternative basket structure that may be utilized in place of basket 300 in extraction device 100 (FIG. 1).

Referring to FIGS. 9-11, in some example embodiments, petal grasper 2300 may include two or more petals 2302, 2304, 2306, 2308. Some example embodiments may include three or more petals 2302, 2304, 2306, 2308, such as four petals 2302, 2304, 2306, 2308. For clarity, FIGS. 10 and 11 illustrate petal 2302 and 2304; however, one of skill in the art will recognize that any other petals (e.g., petals 2306, 2308) may operate in substantially the same manner as petal 2302 and/or petal 2304. Petals 2302, 2304, 2306, 2308 may be mounted to shaft 200 at or near a shaft distal end 201. For example, petals 2302, 2304, 2306, 2308 may be generally evenly circumferentially spaced apart at shaft distal end opening 202. Petals 2302, 2304, 2306, 2308 may be longitudinally slidable (e.g., proximally and/or distally) relative to shaft 200.

In some example embodiments, petals 2302, 2304, 2306, 2308 may be bendable and/or pivotable (compare FIGS. 10 and 11) and/or may be biased to the open configuration (FIGS. 9 and 10). For example, petals 2302, 2304, 2306, 2308 may be formed such that their respective distal tips 2303, 2305, 2307, 2309 are biased generally radially outward (e.g., biased open) to form a grasper distal end opening 2301. In some example embodiments, petals 2302, 2304, 2306, 2308 may be constructed at least partially from nickel titanium alloys (e.g., nitinol) in the super elastic range, for example.

Referring to FIG. 9, some example embodiments may include walls 2316, 2318 disposed on respective petals 2306, 2308. For example, a petal 2306, 2308 that is formed generally as a distally extending loop in a lobed shape may have a wall 2316, 2318 disposed generally within the lobed shaped loop in a generally circumferential fashion. In some example embodiments, walls 2316, 2318 may be constructed from a mesh (e.g., metal wire mesh) and/or an elastomeric film (e.g., which may be laser cut and/or may be porous). Referring to FIGS. 2 and 9, in some example embodiments according to at least some aspects of the present disclosure, walls 312, 314, 316, 318, 320, 2316, 2318 may partially cover a respective leg 302, 304, 306, 308, 310 and/or petal 2302, 2304, 2306, 2308 (see, e.g., wall 2316 in FIG. 9) or fully cover the respective leg 302, 304, 306, 308, 310 and/or petal 2302, 2304, 2306, 2308 (see, e.g., wall 2318 in FIG. 9). It is within the scope of the present disclosure to utilize any wall described herein with any example embodiment described herein.

Referring to FIGS. 1, 10, and 11, in some example embodiments according to at least some aspects of the present disclosure, an actuator line 2322 may extend longitudinally through shaft 200 from actuator 500 on handle 400 to petal grasper 2300. Actuator line 2322 may be operatively coupled to actuator 500 and/or petals 2302, 2304, 2306, 2308 such that when actuator 500 is in an open position, petals 2302, 2304, 2306, 2308 are in the open configuration (FIGS. 9 and 10) and/or when actuator 500 is in a closed position, petals 2302, 2304, 2306, 2308 are in the closed configuration (FIG. 11). In the closed configuration, petals 2302, 2304, 2306, 2308 may be generally drawn together and/or closed, thus at least partially closing grasper distal end opening 2301.

In some example embodiments, in a fully closed configuration, petals 2302, 2304, 2306, 2308 may substantially completely enclose (e.g., encapsulate) object 600 held within petal grasper 2300. For example, distal ends 2303, 2305, 2307, 2309 of petals 2302, 2304, 2306, 2308 may substantially come into contact with one another, thereby substantially closing grasper distal end opening 2301. In some example embodiments, in the closed configuration (FIG. 11), distal ends 2303, 2305, 2307, 2309 of petals 2302, 2304, 2306, 2308 may at least partially overlap one another, and/or may lock together.

In some example embodiments, in a fully closed configuration, petals 2302, 2304, 2306, 2308 may partially enclose object 600 held within petal grasper 2300. In some example embodiments, in a partially closed configuration (e.g., a configuration between the open configuration and the closed configuration), petals 2302, 2304, 2306, 2308 may partially enclose object 600 held within petal grasper 2300.

In some example embodiments, when petal grasper 2300 is in the open configuration (FIGS. 9 and 10), operating actuator 500 from the open position towards the closed position may cause proximal movement of actuator line 2322, which may be tensioned distally by the opening bias of petals 2302, 2304, 2306, 2308. Movement of actuator line 2322 proximally may cause petals 2302, 2304, 2306, 2308 to withdraw at least partially within shaft distal end opening 202, thereby contacting shaft distal end opening 202 and causing petals 2302, 2304, 2306, 2308 to rotate such that distal ends 2303, 2305, 2307, 2309 of petals 2302, 2304, 2306, 2308 to move radially inward, generally circumferentially reducing and/or closing grasper distal end opening 2301. In some example embodiments, in the closed configuration (FIG. 11), petals 2302, 2304, 2306, 2308 may be at least partially within shaft 200 and at least partially extending distally from shaft distal end 201.

In some example embodiments, when petal grasper 2300 is in the closed configuration (FIG. 11), operating actuator 500 from the closed position towards the open position may allow distal movement of actuator line 2322, which may be tensioned distally by the opening bias of petals 2302, 2304, 2306, 2308. Movement of actuator line 2322 distally may allow distal ends 2303, 2305, 2307, 2309 of petals 2302, 2304, 2306, 2308 to move radially outward, generally circumferentially expanding and/or opening grasper distal end opening 2301.

In some example embodiments, petals 2302, 2304, 2306, 2308 may be substantially identical to each other and/or may be arranged generally symmetrically about shaft distal end opening 202. In some example embodiments, one or more petals 2302, 2304, 2306, 2308 may differ from the others and/or may be arranged generally asymmetrically about shaft distal end opening 202.

Referring to FIGS. 1 and 9-11, an example method of operating an extraction device 100 including a petal grasper 2300 is described. In some example methods, a suitable path to the kidney stone in the patient's body is established, and appropriate visualization may also be established, such as by means of a ureteroscope. Thereafter, extraction device 100 is advanced until petal grasper 2300 reaches the targeted area where object 600 to be removed is located. In some example embodiments, this advance may be accomplished by manually feeding shaft 200 through a working channel in the ureteroscope.

Upon reaching object 600, petal grasper 2300 is placed in the open configuration (FIGS. 9 and 10), if it is not already in the open configuration. For example, in some circumstances it may be desirable to insert extraction device 100 with petal grasper 2300 in the closed configuration. Then, extraction device 100 may be manipulated to position object 600 (e.g., a kidney stone) generally within petal grasper 2300. Then, actuator 500 may be operated to withdraw proximally actuator line 2322, which may cause petals 2302, 2304, 2306, 2308 to withdraw at least partially within shaft distal end opening 202, thereby contacting shaft distal end opening 202 and causing petals 2302, 2304, 2306, 2308 to rotate such that distal ends 2303, 2305, 2307, 2309 of petals 2302, 2304, 2306, 2308 to move radially inward, generally circumferentially reducing and/or closing grasper distal end opening 2301 and/or at least partially capturing object 600 within petal grasper 2300 (FIG. 11). With object 600 retained petal grasper 2300, extraction device 100 may be removed from the patient, thereby removing object 600 from the patient.

In some example embodiments according to at least some aspects of the present disclosure, shafts 200, 1200 may be fabricated to provide a generally smooth exterior periphery and a hollow interior. For example, shaft 200, 1200 and/or outer sheath 1206 may comprise a multilayer construction, which may include an outer layer of polytetrafluoroethylene (e.g., Teflon), a polyimide layer, a stainless-steel braid layer, and/or an inner polyimide layer demarcating a hollow interior. Shafts 200, 1200 and/or outer sheath 1206 may have a substantially constant cross-section or a cross-section that changes along its longitudinal length.

Moreover, shafts 200, 1200 and/or outer sheath 1206 may have a circular cross-section, an oblong cross-section, or any other shaped cross-section that provides a longitudinal conduit therethrough.

In some example embodiments according to at least some aspects of the present disclosure, closure lines 322, 1322 and/or actuator line 2322 may be constructed at least partially of metal wire and/or cable. In some example embodiments, closure lines 322, 1322 may be constructed at least partially of suture material.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope. Various characteristics and features described herein are designed to be combined with one another and utilized in connection with other embodiments described herein. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

The invention claimed is:

1. An extraction device, comprising:
   a generally tubular shaft comprising a distal end configured to be inserted into a patient and a proximal end configured to be retained exteriorly of the patient;
   a basket extending from the distal end of the generally tubular shaft, the basket comprising a plurality of flexible, distally extending legs each having a lobed shape, the plurality of flexible, distally extending legs including respective distal ends that are biased generally radially outward to at least partially define a basket distal opening;
   a handle disposed at the proximal end of the generally tubular shaft;
   an actuator disposed on the handle; and
   a closure line operatively coupled to the actuator, the closure line extending distally through the generally tubular shaft, through a closure line guide disposed on the distal end of the generally tubular shaft, and generally circumferentially about the basket distal opening, the closure line being slidably coupled to each leg near its respective leg distal end;
   wherein the actuator is operative between an open position and a closed position to extend and withdraw the closure line, thereby moving the basket between an open configuration and a closed configuration, respectively.

2. The extraction device of claim 1, further comprising at least one generally circumferential wall disposed on at least one of the plurality of flexible, distally extending legs.

3. The extraction device of claim 2, wherein the at least one generally circumferential wall comprises at least one of a wire mesh and an elastomeric film.

4. The extraction device of claim 1, wherein at least two of the plurality of flexible, distally extending legs are substantially identical to each other and are disposed substantially symmetrically on the generally tubular shaft.

5. The extraction device of claim 1, wherein the closure line guide is generally tubular, slidably receives the closure line therein, and extends substantially from the distal end of the generally tubular shaft to the distal end of one of the plurality of flexible, distally extending legs.

6. The extraction device of claim 1, wherein at least one of the plurality of flexible, distally extending legs comprises a distally extending, lobe-shaped loop.

7. The extraction device of claim 1, further comprising a lock on the handle, the lock being operatively coupled to the actuator to lock the actuator in at least one of the open position and the closed position.

8. The extraction device of claim 1, wherein the closure line is slidably coupled to each leg near its respective leg distal end in a draw-string fashion.

9. The extraction device of claim 1, wherein the closure line guide is flexible so that the closure line guide is bent radially inward when the basket is in the closed configuration.

10. A method of operating an extraction device, the method comprising:
    advancing the extraction device into a patient's body until a basket of the extraction device reaches a targeted area containing an object, the basket comprising a plurality of flexible, distally extending legs each having a lobed shape, the plurality of flexible, distally extending legs including respective distal ends that are biased generally radially outward to at least partially define a basket distal opening;
    manipulating the extraction device to position the object at least partially within the basket; and
    capturing the object by at least partially closing the basket distal opening by withdrawing proximally a closure line, the closure line extending through a closure line guide and generally circumferentially about the basket distal opening, the closure line being slidably coupled to each leg near its respective leg distal end, the closure line drawing together the legs respective distal ends in a draw-string fashion.

11. The method of claim 10, further comprising, after capturing the object, removing the extraction device and the object from the patient's body.

12. The method of claim 10, further comprising, prior to manipulating the extraction device to position the object at least partially within the basket, placing the basket into an open configuration by moving the closure line distally.

13. The method of claim 10,
    wherein the extraction device comprises
    a generally tubular shaft comprising a distal end configured to be inserted into the patient's body and a proximal end configured to be retained exteriorly to the patient's body, and
    a handle disposed at the proximal end of the generally tubular shaft;
    wherein the basket extends form the distal end of the generally tubular shaft;
    wherein the closure line guide is disposed on the distal end of the generally tubular shaft; and
    wherein withdrawing proximally the closure line comprises withdrawing the closure line proximally through the closure line guide and the generally tubular shaft by operating an actuator disposed on the handle.

14. The method of claim 10, wherein advancing the extraction device into the patient's body includes advancing the extraction device through a working channel in a ureteroscope.

15. The method of claim 10,
    wherein the extraction device comprises at least one generally circumferential wall disposed on at least one of the plurality of flexible, distally extending legs; and
    wherein capturing the object includes capturing the object using the at least one generally circumferential wall.

16. The method of claim 10, wherein at least partially closing the basket distal opening comprises bending the closure line guide radially inward.

* * * * *